(12) United States Patent
Ghelli et al.

(10) Patent No.: US 11,123,469 B2
(45) Date of Patent: Sep. 21, 2021

(54) BLOOD FILTERING DEVICE

(71) Applicant: EUROSETS S.R.L., Medolla (IT)

(72) Inventors: Nicola Ghelli, Medolla (IT); Edgardo Costa Maianti, Medolla (IT); Roberto Balanzoni, Medolla (IT); Antonio Petralia, Medolla (IT)

(73) Assignee: EUROSETS S.R.L., Medolla (IT)

( * ) Notice: Subject to any disclaimer, the term of this patent is extended or adjusted under 35 U.S.C. 154(b) by 0 days.

(21) Appl. No.: 16/646,076

(22) PCT Filed: Sep. 25, 2018

(86) PCT No.: PCT/IB2018/057402
§ 371 (c)(1),
(2) Date: Mar. 10, 2020

(87) PCT Pub. No.: WO2019/058355
PCT Pub. Date: Mar. 28, 2019

(65) Prior Publication Data
US 2020/0254171 A1   Aug. 13, 2020

(30) Foreign Application Priority Data

Sep. 25, 2017   (IT) .................. 102017000107088

(51) Int. Cl.
*A61M 1/36* (2006.01)
*B01D 29/31* (2006.01)
(Continued)

(52) U.S. Cl.
CPC .......... *A61M 1/3635* (2014.02); *B01D 23/06* (2013.01); *B01D 27/142* (2013.01); *B01D 29/005* (2013.01); *B01D 29/23* (2013.01)

(58) Field of Classification Search
CPC .............. A61M 1/3635; A61M 1/3632; A61M 1/3666; A61M 2205/7545;
(Continued)

(56) References Cited

U.S. PATENT DOCUMENTS 4,648,971 A   3/1987 Pabst
5,411,705 A   5/1995 Thor et al.
(Continued)

FOREIGN PATENT DOCUMENTS

EP   2 545 948 A1   1/2013
JP   2002 165878 A   6/2002

*Primary Examiner* — Krishnan S Menon
(74) *Attorney, Agent, or Firm* — Aslan Law, P.C.

(57) ABSTRACT

A blood filtering device comprises a casing defining a containment volume and provided with at least a first inlet for the venous blood, at least a second inlet for the intracavitary blood, at least a third inlet for the extra cavitary blood and at least an outlet mouth for the blood; blood filtering means which are housed inside the containment volume and delimiting at least one filtering volume communicating with the blood inlets and at least one collecting volume communicating with the outlet mouth; where filtering means comprise: at least a first filtering element defining a closed profile and delimiting a first filtering volume communicating with the first inlet; at least a second filtering element defining a closed profile and delimiting a second filtering volume communicating with the second inlet; at least a third filtering element defining a closed profile and delimiting a third filtering volume communicating with the third inlet.

20 Claims, 9 Drawing Sheets

(51) Int. Cl.
  *B01D 27/14* (2006.01)
  *B01D 29/00* (2006.01)
  *B01D 29/23* (2006.01)
(58) Field of Classification Search
  CPC . A61M 2206/14; A61M 1/3627; B01D 29/23; B01D 29/005; B01D 27/142; B01D 23/06
  See application file for complete search history.

(56) References Cited

U.S. PATENT DOCUMENTS

| | | | | |
|---|---|---|---|---|
| 5,770,073 A * | 6/1998 | Bach | ............ | A61M 1/3627 210/472 |
| 6,017,493 A * | 1/2000 | Cambron | ............ | A61M 1/36 422/44 |
| 6,287,270 B1 * | 9/2001 | Fini | ............ | A61M 1/3627 604/6.15 |
| 7,476,359 B2 * | 1/2009 | Maianti | ............ | A61M 1/3627 422/46 |
| 7,591,812 B1 * | 9/2009 | Tamari | ............ | A61M 1/3627 422/44 |
| 7,749,435 B2 * | 7/2010 | Ogihara | ............ | A61M 1/1698 422/46 |
| 8,147,440 B2 * | 4/2012 | Tamari | ............ | A61M 1/3638 604/6.15 |
| 8,157,103 B2 * | 4/2012 | Eagle | ............ | A61M 1/0001 210/359 |
| 8,597,417 B2 * | 12/2013 | Kobayashi | ............ | A61M 1/3627 96/219 |
| 8,986,238 B2 * | 3/2015 | Robinson | ............ | A61M 1/0281 604/6.09 |
| 9,011,769 B2 * | 4/2015 | Silvestri | ............ | A61M 1/1698 422/45 |
| 9,545,472 B2 * | 1/2017 | Gloss | ............ | B01D 35/02 |
| 2002/0094300 A1 * | 7/2002 | Yokoyama | ............ | A61M 1/3627 422/44 |

* cited by examiner

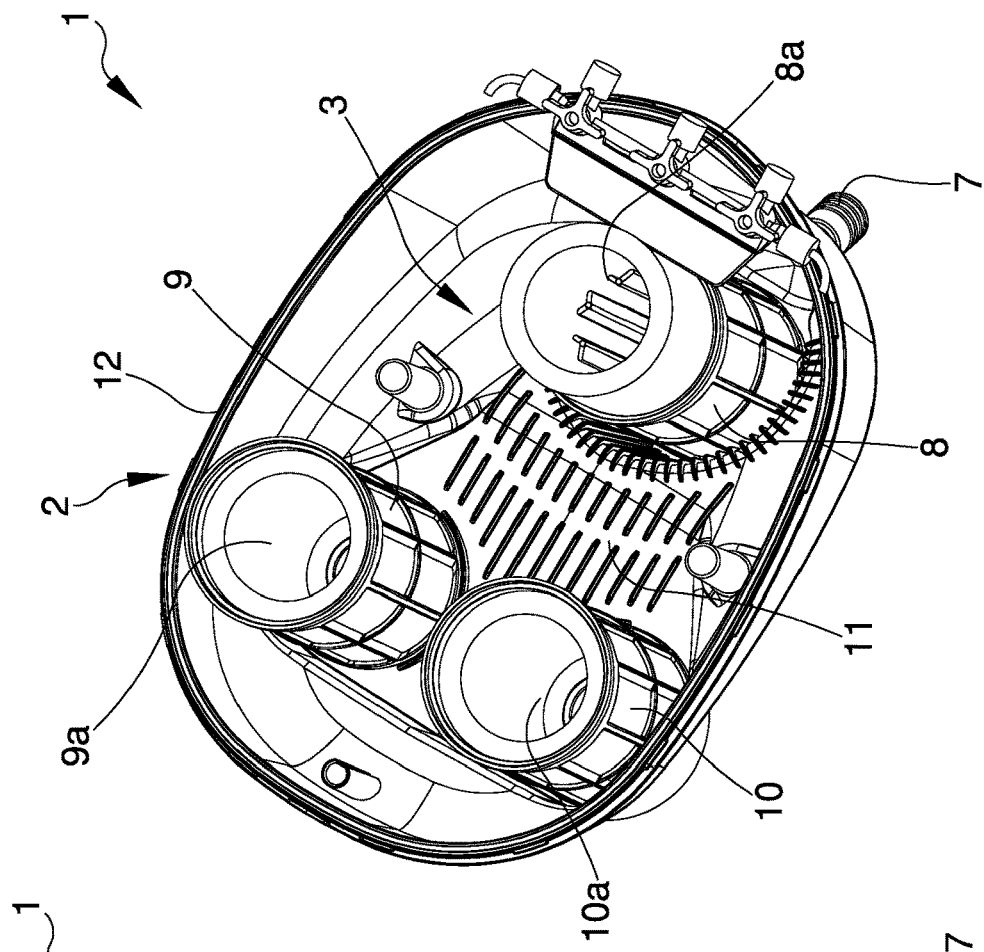
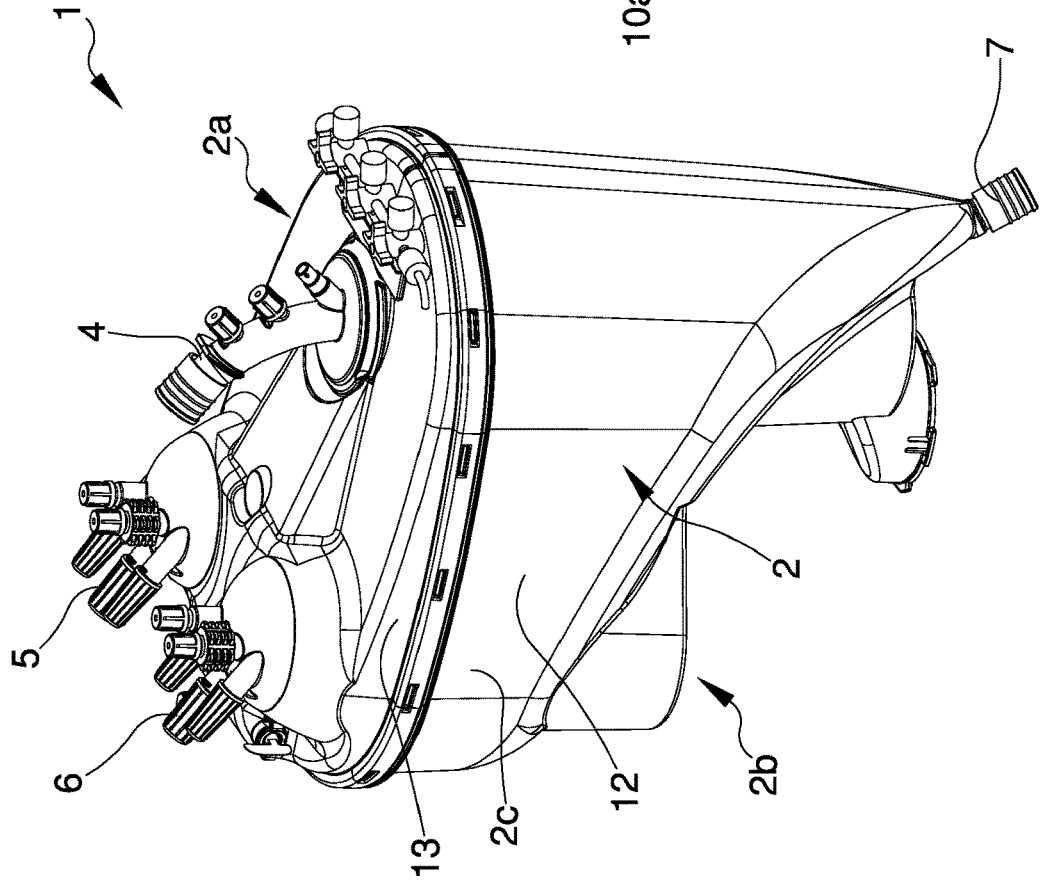
Fig.1
Fig.2

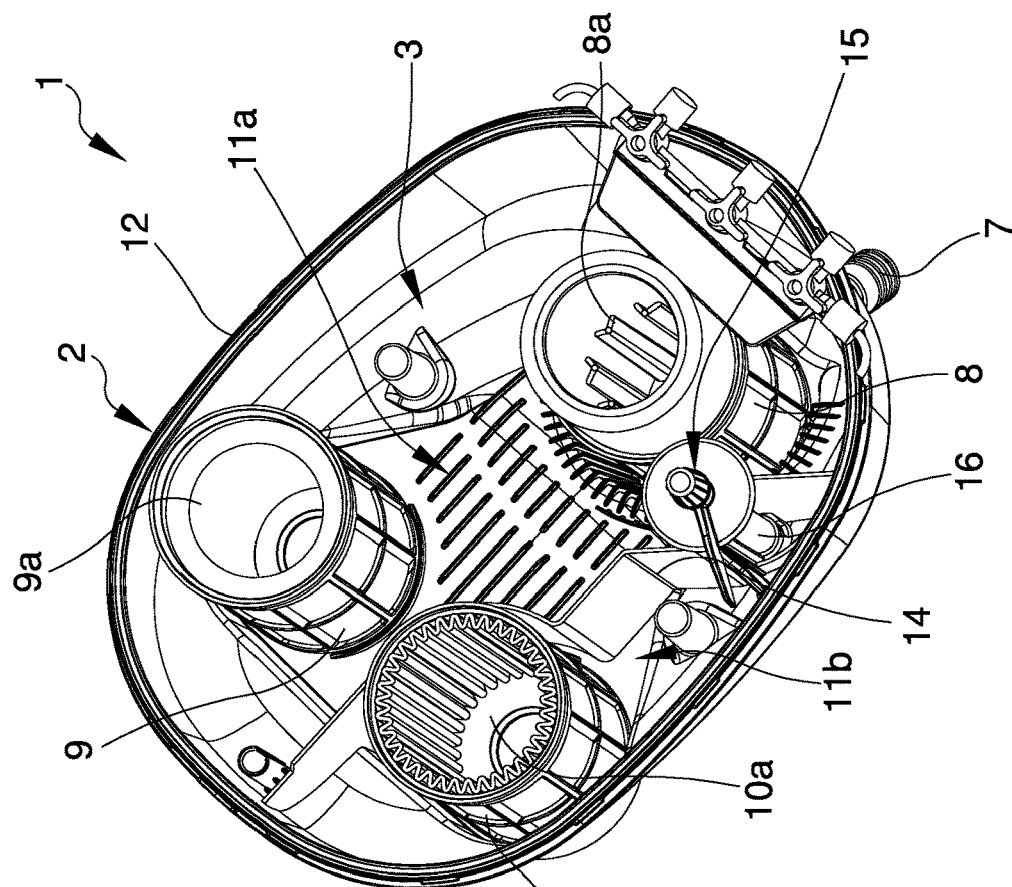
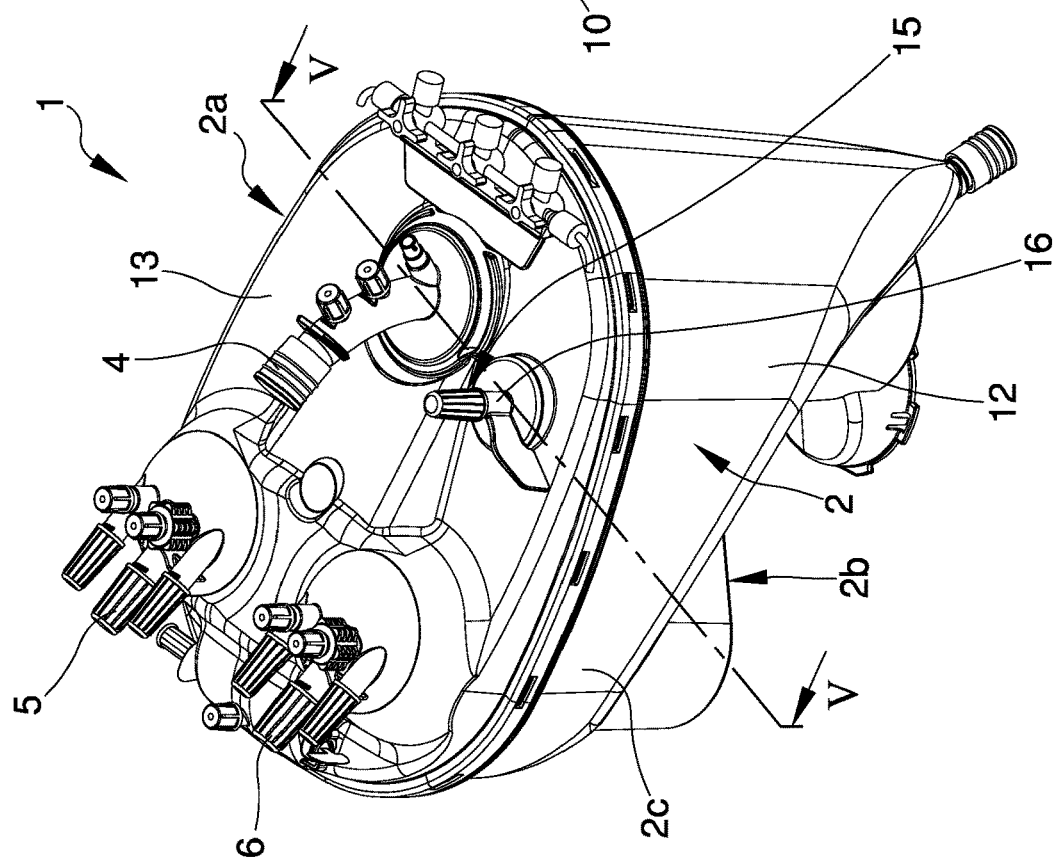
Fig.4
Fig.3

BLOOD FILTERING DEVICE

CROSS-REFERENCE TO RELATED APPLICATIONS

This application is a National Stage Entry of PCT/IB2018/057402 filed on Sep. 25, 2018. This application claims priority to IT Patent Application No. 102017000107088 filed on Sep. 25, 2017, and to PCT Application No. PCT/IB2018/057402 filed on Sep. 25, 2018, the entire contents of which are hereby incorporated by reference

TECHNICAL FIELD

The present invention relates to a blood filtering device in extracorporeal blood circuit.

BACKGROUND ART

As is known, during certain surgical operations, when the functions of the patient's heart are temporarily interrupted, extracorporeal blood circuits are made which use so-called "heart-lung" machines.

The heart-lung machines comprise a series of devices of which a filtering device (also referred to as "venous reservoir") adapted to filter the blood coming from the patient, a heat exchanger adapted to regulate the temperature of the blood leaving the filtering device, and an oxygenator adapted to provide the correct supply of oxygen to the blood intended to be reintroduced into the patient.

More particularly, during extracorporeal circulation (ECC) the blood drains by gravity or due to the effect of the application of a negative pressure inside the venous reservoir of the heart-lung machine passing through the cannulae positioned in the hollow veins or through a cannula positioned in the right atrium. From the venous reservoir the blood is pumped into the arterial system, usually through a cannula positioned in the ascending aorta, passing through a membrane oxygenator where the blood is oxygenated and decarboxylated.

This system can be used to provide total or partial circulatory and respiratory assistance.

The extracorporeal blood circuits are completed by the field aspiration lines (aortic root, vent, field aspirator), the cardioplegia infusion line, a filter for emboli and bubbles, and a heat exchanger.

The filtering devices present in the venous reservoir are used to eliminate the emboli in the extracorporeal circuit which can be either in gaseous or solid form.

The main sources of solid emboli are essentially the frustules of the surgical operation field that comprise atheromas, calcium, lipids, bone fragments, denatured proteins, suture materials, platelet and leukocyte aggregates.

The main source of the gaseous emboli that enter the extracorporeal circuit is the surgical field. Air can be aspirated from the site of venous cannulation, during aortic cannulation, during aspirations from the aortic root, from the vent, from the field aspirator.

The filtering devices known as of today comprise a rigid casing provided with an upper cover at which blood inlet unions are defined, of which a union adapted to receive the so-called "intracavitary" blood coming directly from the patient's heart and a union adapted to receive "extracavitary" blood. This device then has a further union adapted to receive the blood coming from a patient's vein, generally arranged at the bottom of the casing, and an outlet mouth of the filtered blood.

More particularly, inside the casing there is a filtering element, defining a closed profile, the internal volume of which is placed in communication with the above-mentioned blood inlet unions and the external volume of which is placed in communication with the outlet mouth of the filtered blood. The blood entering the casing then passes through the filtering element and exits from the outlet mouth.

These filtering devices of known type do have a number of drawbacks.

These in fact do not allow an effective filtration of the treated blood.

As known, in fact, the intracavitary blood and the extracavitary blood aspirated during the cardiac surgery operations have considerably different properties from each other, in fact, while the intracavitary blood is generally not very activated (i.e. without solid emboli) and with a reduced number of air bubbles, the extracavitary blood is very activated and rich in air bubbles.

Since in the devices of known type the intracavitary blood (with few gaseous emboli) and the extracavitary one (with many gaseous emboli) are mixed together before being filtered, it follows that this involves an activation of the intracavitary blood, which is then "contaminated" by the extracavitary one. The filtration carried out by the devices of known type is therefore not very effective since the filtering element, having to eliminate both emboli in the gaseous and those in the solid form, reduces the elimination capacity of gaseous micro-emboli and also the blood filtration capacity.

DESCRIPTION OF THE INVENTION

The main aim of the present invention is to devise a blood filtering device which allows improving the efficiency of filtration with respect to devices of known type.

In particular, the present invention intends to optimize the filtration for each flow of treated blood, so as to improve the quality of the output blood.

A further object of the present invention is to devise a blood filtering device which allows overcoming the aforementioned drawbacks of the prior art within the scope of a simple, rational, easy, efficient to use and cost-effective solution.

The aforementioned objects are achieved by the present blood filtering device according to claim 1.

BRIEF DESCRIPTION OF THE DRAWINGS

Other characteristics and advantages of the present invention will become more evident from the description of a preferred, but not exclusive embodiment of a blood filtering device, illustrated by way of an indicative, but non-limiting example, in the attached drawings in which:

FIG. 1 is an axonometric view of a device according to the invention, in a first embodiment;

FIG. 2 is a top axonometric view of a part of the device of FIG. 1;

FIG. 3 is an axonometric view of a device according to the invention, in a second embodiment;

FIG. 4 is a top axonometric view of a part of the device of FIG. 3;

EMBODIMENTS OF THE INVENTION

Figure 5:
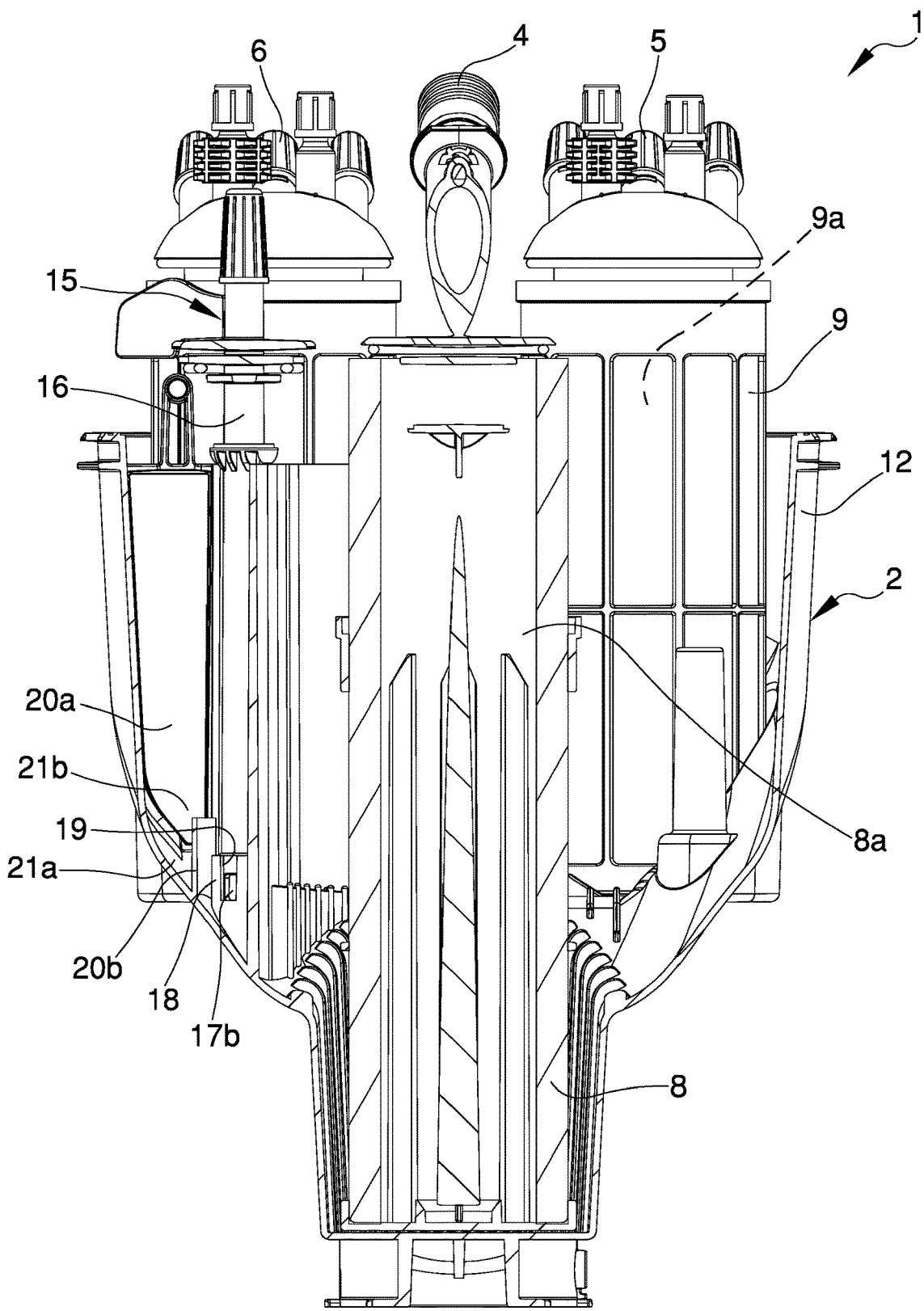
FIG. 5 is a sectional view of a part of the device of FIG. 3 along the track plane V-V.

With particular reference to these figures, reference numeral 1 globally indicates a blood filtering device.

The device 1 comprises a casing 2 which defines a containment volume 3 and (the casing) is provided with at least a first inlet 4 for the venous blood coming from the patient, at least a second inlet 5 for the intracavitary blood (with few gaseous emboli), at least a third inlet 6 for the extracavitary blood (rich in gaseous emboli) and at least an outlet mouth 7 for the blood.

Inside the containment volume 3 are housed blood filtering means 8, 9, 10 which delimit at least one filtering volume 8a, 9a, 10a communicating with the blood inlets 4, 5, 6 and at least one collecting volume 11 communicating with the outlet mouth 7.

According to the invention, the filtering means 8, 9, 10 comprise at least a first filtering element 8 which defines a closed profile and delimits a first filtering volume 8a communicating with the first inlet 4, a second filtering element 9, which defines a closed profile and delimits a second filtering volume 9a communicating with the second inlet 5, and a third filtering element 10 which defines a closed profile and delimits a third filtering volume 10a communicating with the third inlet 6, where the first, the second and the third filtering elements 8, 9, 10 are separated and distinct from each other.

As can easily be understood, depending on the specific requirements of the case, the filtering elements 8, 9, 10 may be of a different type, so that their filtering characteristics are selected according to the type of blood to be filtered. The casing 2 has an upper portion 2a, a bottom wall 2b and a side wall 2c.

Preferably, the inlets 4, 5, 6 are defined at the upper portion 2a.

Conveniently, the outlet mouth 7 is defined at the bottom wall 2b.

As can be seen in FIGS. 1 and 3, the casing 2 comprises a body 12 open at the top, defining the side wall 2c and the bottom wall 2b, and a cover 13 to close the body 12 defining the upper portion 2a at which are defined the inlets 4, 5, and 6.

More particularly, the second and third inlets 5, 6 are defined by a covering element 28 which engages with a corresponding supporting element 29 associated with the upper portion 2a, where at least one sealing element 30 is interposed between the covering element 28 and the supporting element 29.

Advantageously, the filtering elements 8, 9 and 10 have a tubular shape, the lower base of which is located at the bottom wall 2b and the upper base of which is placed in communication with the corresponding inlet 4, 5 and 6. A containment element 31 is located around the filtering elements 8, 9 and 10.

In the embodiments shown in the figures, the second and third filtering element 9, 10 are arranged side by side.

More particularly, the first filtering element 8 has a longer longitudinal extension than the second and the third filtering elements 9 and 10.

As can be seen from the figures, in fact, the bottom wall 2b has a first stretch, at which are located the bottom extremity of the first filtering element 8 and the outlet mouth 7, and a second stretch, at which are located the bottom extremities of the second and of the third filtering elements 9 and 10, where the first stretch is arranged, in use, at a lower level than the second stretch.

Preferably, the first filtering element 8 is interposed between the outlet mouth 7 and the second and third filtering element 9 and 10.

Figure 10:
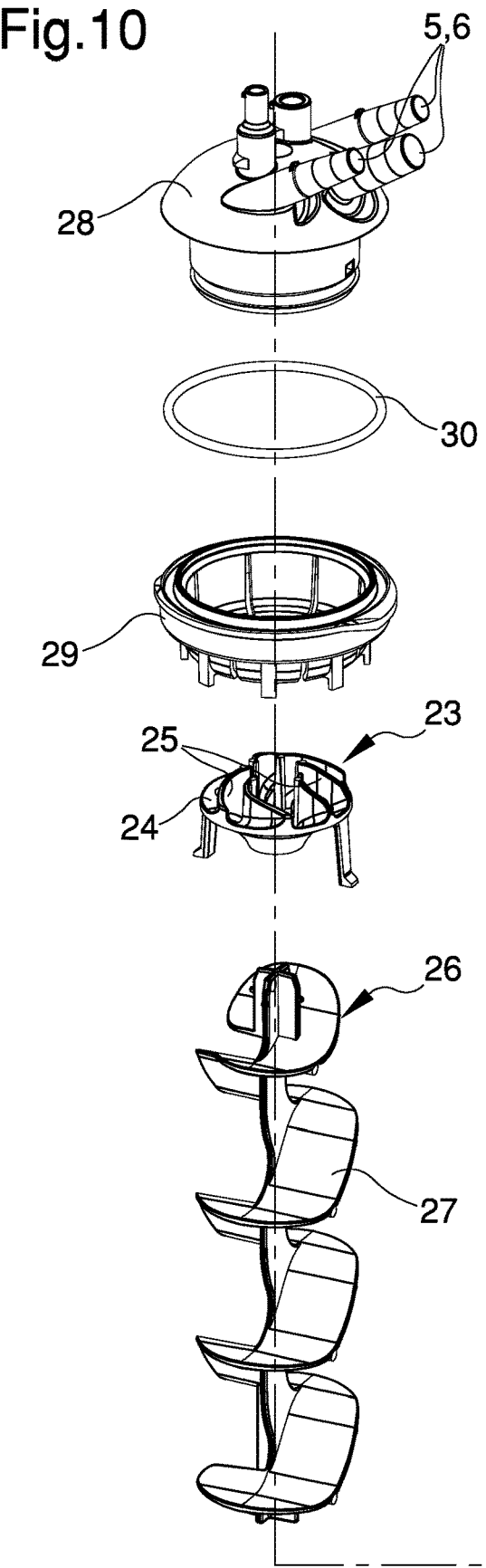
FIG. 10 is an exploded view of a filtering element of a device according to the invention in an alternative embodiment.
Figure 10:
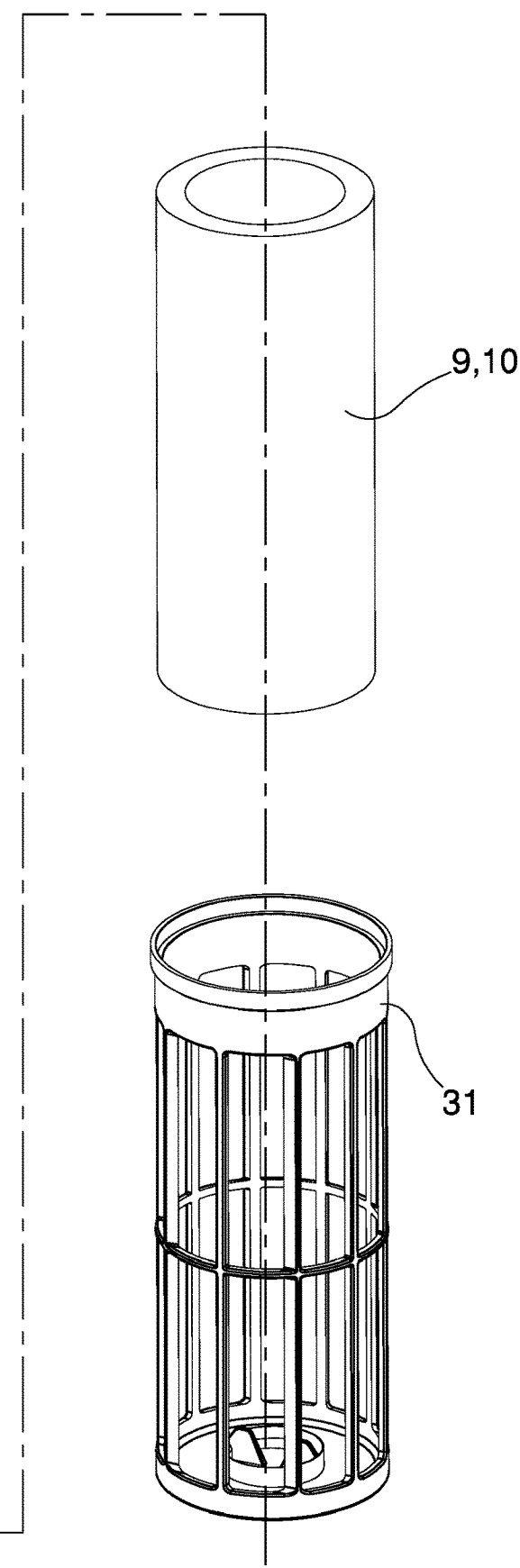
Figure 11:
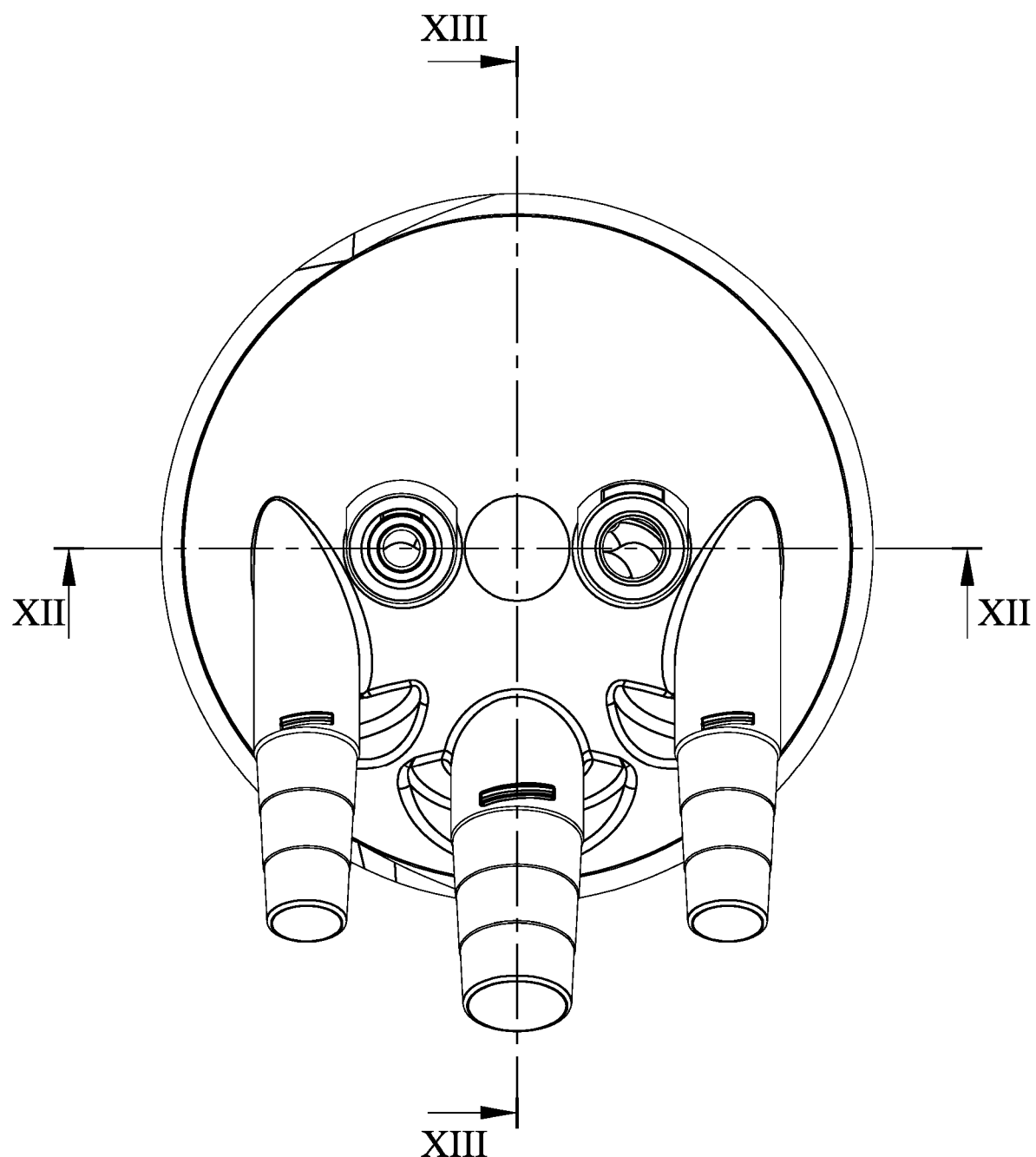
FIG. 11 is a plan view from above of the filtering element of FIG. 10.
Figure 12:
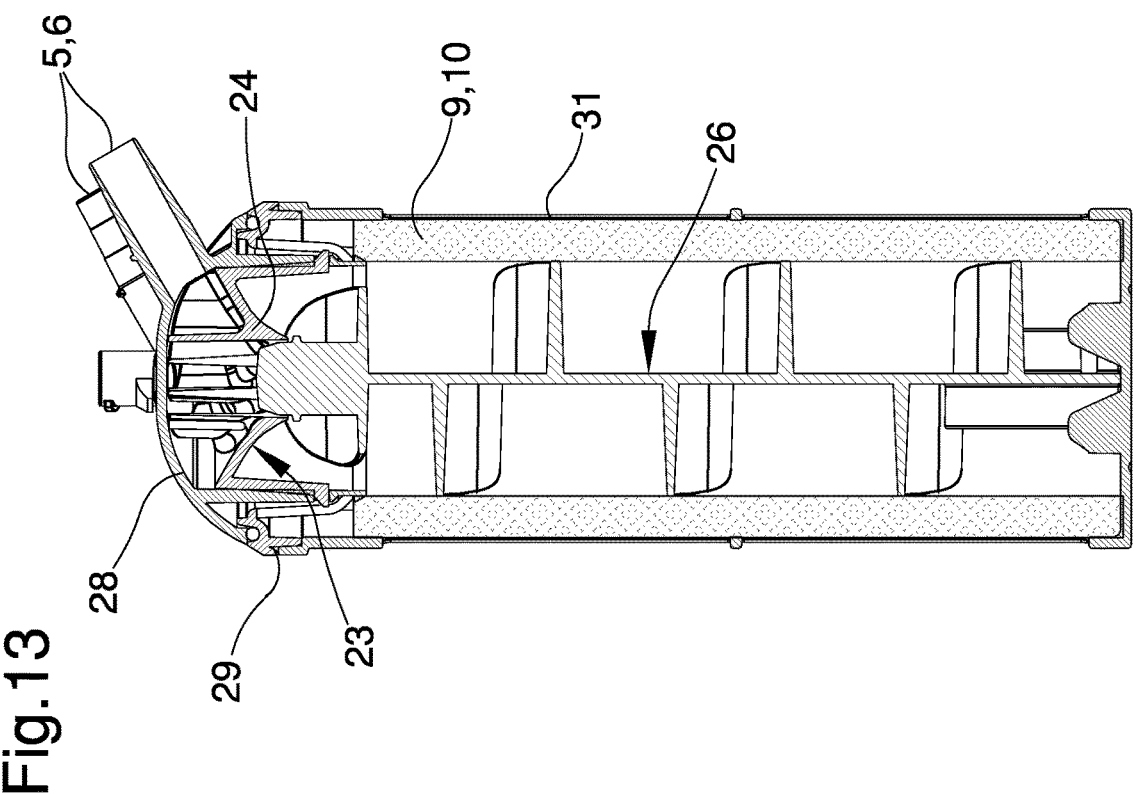
FIG. 12 is a sectional view of the filtering element of FIG. 11 according to the track plane XII-XII.
Figure 13:
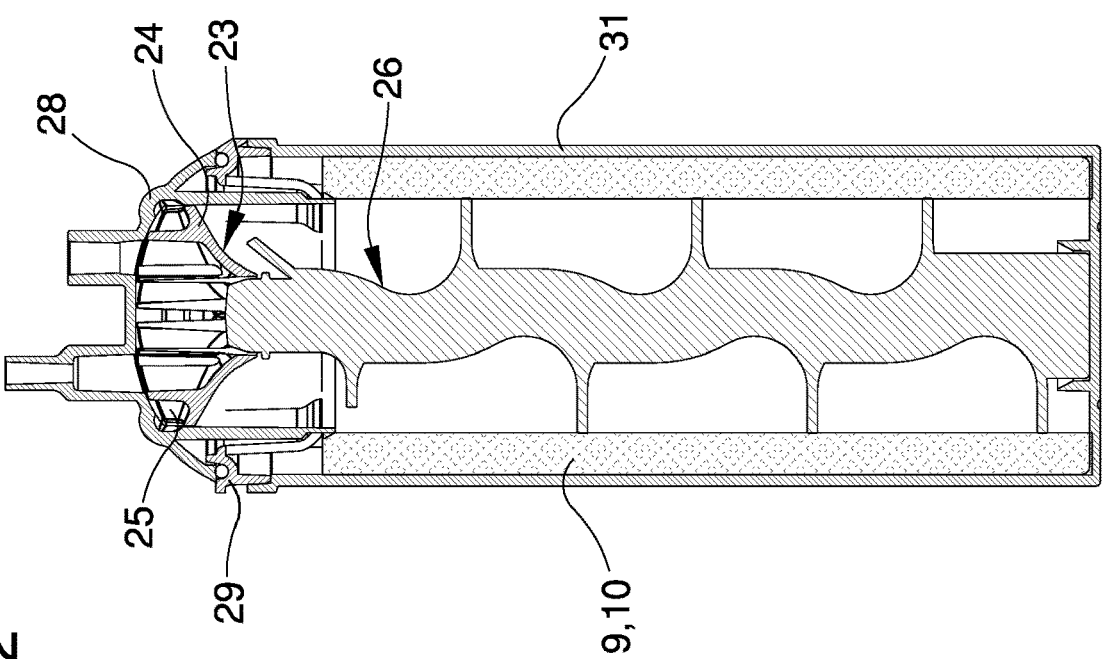
FIG. 13 is a sectional view of the filtering element of FIG. 11 according to the track plane XIII-XIII.

In the embodiment shown in FIGS. 10 to 13, the device 1 comprises a plurality of second and/or third inlets 5, 6 and comprises blood separation means 23 located at at least one of the second and third inlets 5, 6 and communicating with the corresponding filtering volume 9a, 10a, where these separation means 23 are adapted to keep the blood flows coming from the respective inlets 5, 6 separated from each other.

More particularly, the separation means 23 are the type of a body 24 defining a plurality of channels 25 having curvilinear extension, each of which is adapted to receive the flow of blood entering a relative inlet 5, 6 to convey it from a peripheral area towards the center.

The separation means 23 allow preventing the various blood flows entering each inlet 5, 6 from mixing with each other and thus obtaining an initial separation of the air from the blood.

Preferably, the channels 25 have a section converging towards the center.

Advantageously, inside at least one of the second and the third filtering element 9, 10, at least one conveying element 26 is housed, which is adapted to guide the blood along a predefined path so as to convey it towards the corresponding filtering element 9, 10.

In the embodiment shown in the figures, the conveying element 26 is substantially screw-shaped.

More in detail, the conveying element 26 has a blood flowing surface 27 which defines a substantially helical path, the side edge of which is substantially tangent to the internal lateral surface of the corresponding filtering element 9, 10.

The conveying element 26 is arranged below the separation means 23 and is therefore adapted to receive the blood coming from the separation means.

More particularly, the conveying element 26 is interposed between the separation means 23 and the bottom wall 2b.

In the first embodiment shown in FIGS. 1 and 2, the external volumes of each filtering element 8, 9, 10 are communicating with each other. In other words, the collecting volume 11 externally surrounds each filtering element 8, 9, 10 without interruption. This entails the fact that the blood portions entering the casing 2 through the inlets 4, 5 and 6, once filtered, are mixed together, accumulating in the collecting volume 11, and then exit through the outlet mouth 7.

Figure 6:
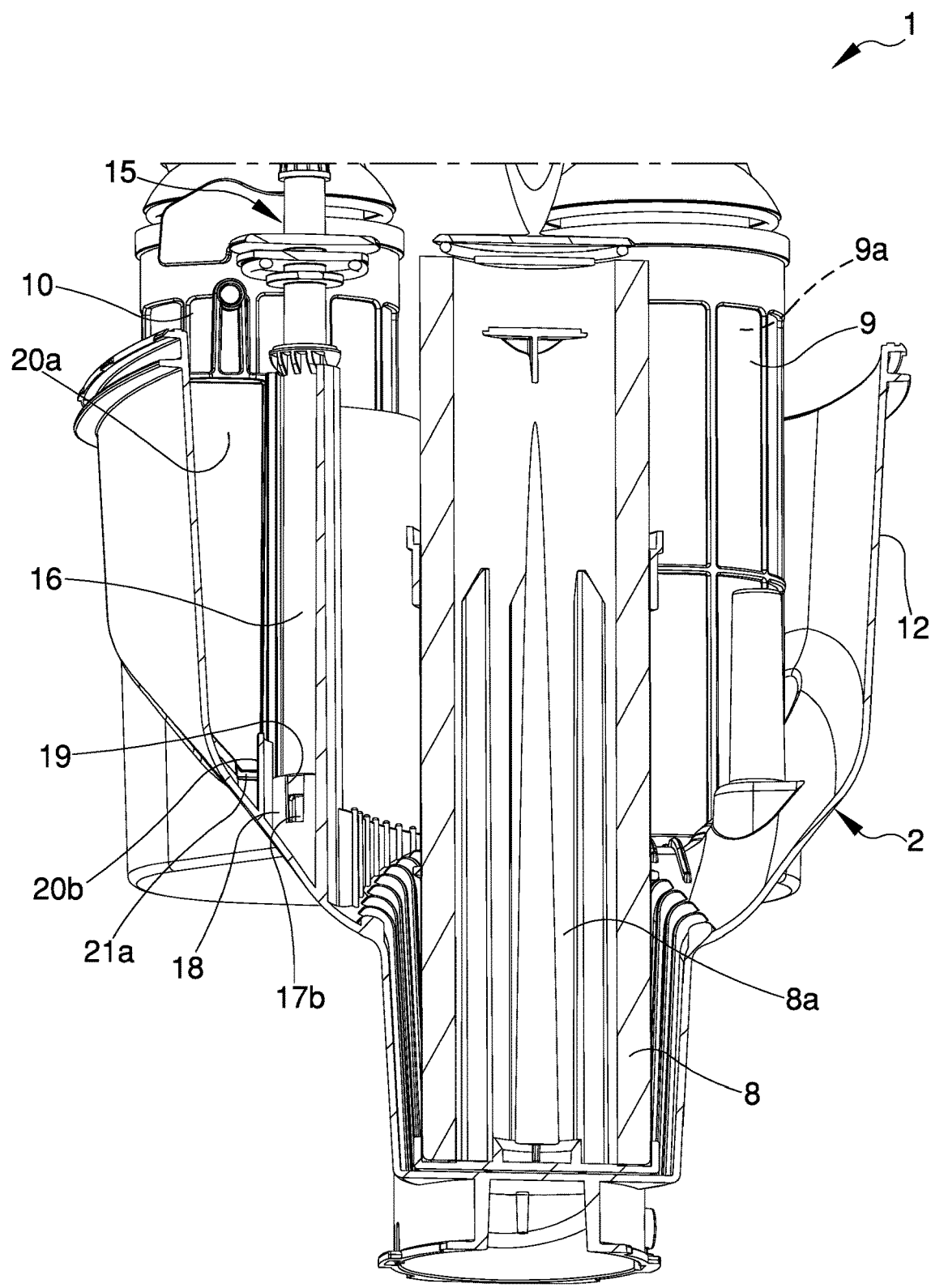
FIG. 6 is an axonometric view of a portion of the section of FIG. 5.
Figure 7:
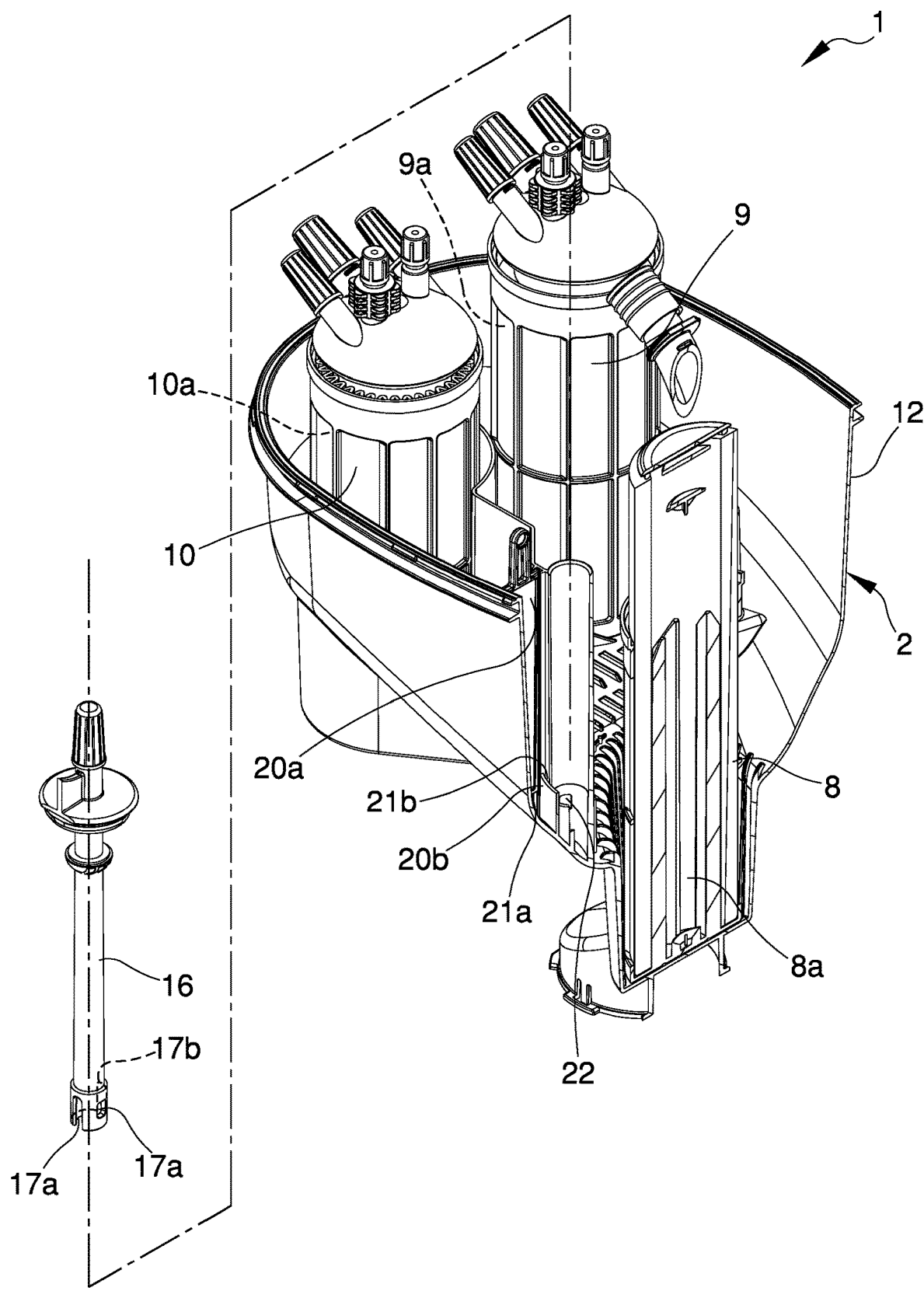
FIG. 7 is a further axonometric view, in partially exploded view, of the section of FIG. 5.
Figure 8:
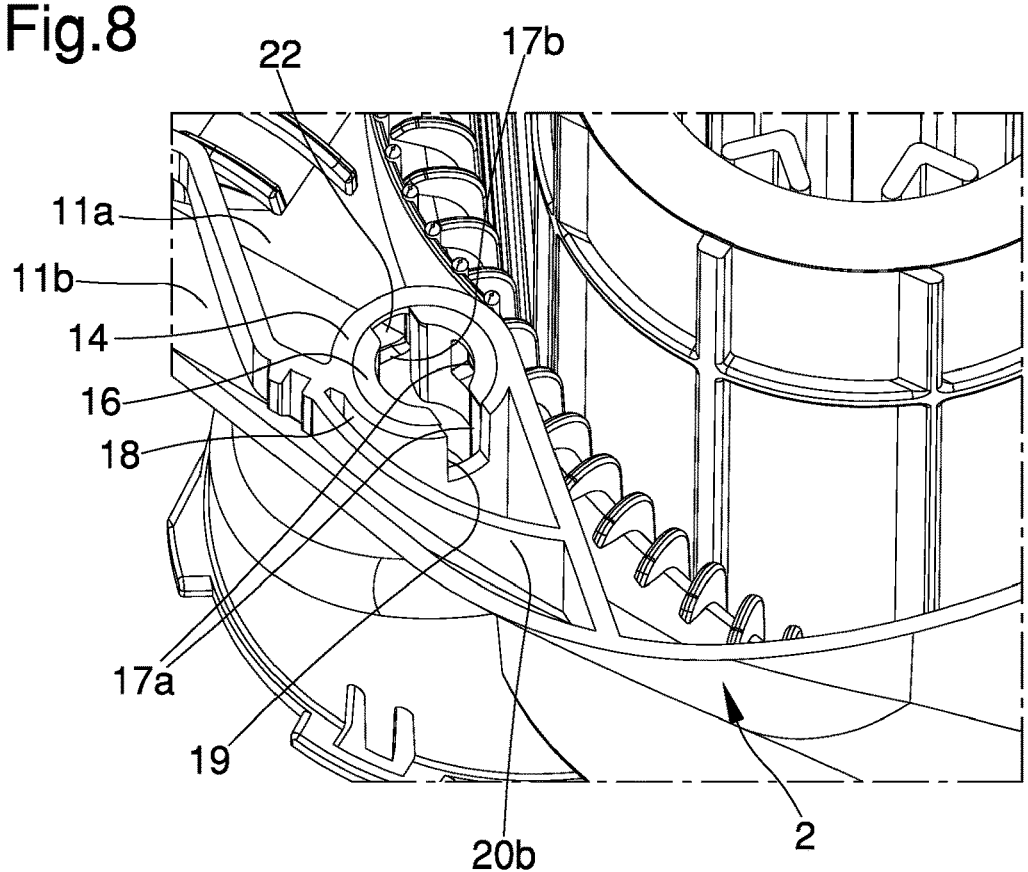
FIGS. 8 and 9 are two cross-sections of the device of FIG. 3 with the relative sleeve in the opening and closing configuration, respectively.
Figure 9:
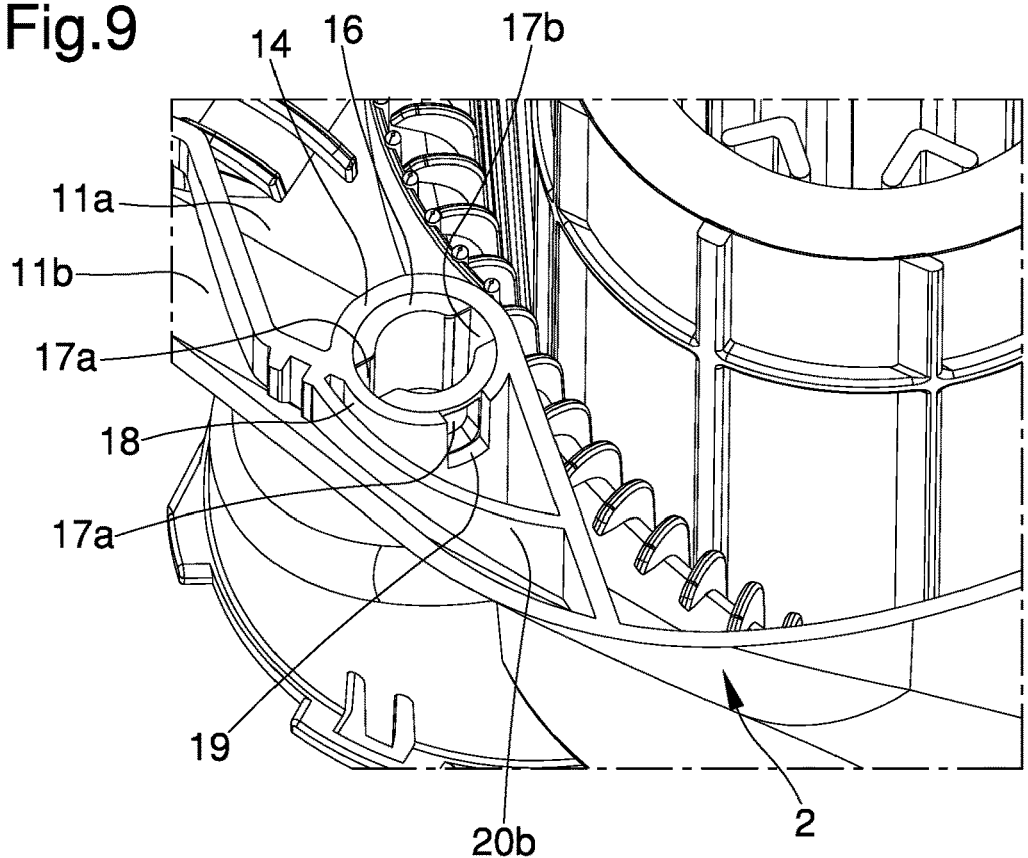

In the second embodiment shown in FIGS. 3 to 6, on the other hand, the device 1 comprises at least one separation wall 14 positioned inside the collecting volume 11, which operates in conjunction with the casing 2 to divide the collecting volume itself into a first collecting volume 11a surrounding the first and second filtering element 8, 9 and communicating with the outlet mouth 7, and into a second collecting volume 11b surrounding the third filtering element 10 and communicating with a blood drawing union 15 separate from the outlet mouth 7. The separation wall 14 thus isolates the third filtering element 10 from the first and the second filtering elements 8 and 9, thus avoiding the mixing of the relative filtered blood portions.

Conveniently, the drawing union 15 comprises a sleeve 16, the top extremity of which protrudes from the cover 13 and is accessible from the outside and the bottom extremity of which is arranged inside the second collecting volume itself.

The sleeve 16 comprises at least a first opening 17a communicating with the second collecting volume 11b and at least a second opening 17b adapted to place the sleeve itself in communication with the first collecting volume 11a, through a passage 22 defined on the separation wall 14 and positioned at the sleeve 16. Conveniently, the sleeve 16 is operable in rotation around a relevant axis between an opening configuration, in which the second opening 17b is placed in communication with the passage 22, and a closure configuration, in which the second opening 17b is isolated from the passage 22, the latter being hindered by the wall of the sleeve itself, so as to maintain the first collecting volume 11a isolated from the second collecting volume 11b. Both in the opening configuration and closure configuration the first opening 17a is placed in communication with the second collecting volume 11b.

In the embodiment shown in the illustrations, the sleeve 16 comprises two first openings 17a and a second opening 17b, which is substantially aligned with one of the first openings 17a, the other first opening 17a being interposed therebetween.

In the opening configuration of the sleeve 16 the first and second collecting volumes 11a and 11b are communicating with each other, so that the operator can then aspirate the blood from the first collecting volume 11a, while in the closure configuration the first and second collecting volumes 11a and 11b are isolated from each other and the operator can aspirate the blood filtered by the third filtering element 10 through the sleeve itself.

Preferably, inside the second collecting volume 11b is provided an appendix 18 extending from the bottom wall 2b, which is adapted to operate in conjunction with the sleeve 16 and provided with at least one recess 19. In more detail, in the opening configuration of the sleeve 16, the first opening 17a and the second opening 17b which are aligned with each other, are positioned at the recess 19 and at the passage 22 respectively, so as to allow the flow of the filtered blood from the second collecting volume 11b inside the sleeve itself and from this inside the first collecting volume 11a, while in the closure configuration the second opening 17b is isolated by the passage 22, which is therefore closed by the side wall of the sleeve 16, thus allowing the operators to aspirate the filtered blood and contained in the second collecting volume 11b through the sleeve itself.

Advantageously, in this second embodiment, inside the second collecting volume 11b at least two break walls 20a, 20b are provided, interposed between the third filtering element 10 and the drawing union 15. More particularly, the break walls 20a, 20b define respective passage gaps 21a, 21b of the blood filtered by the third filtering element 10 positioned at different heights with respect to the bottom wall 2b.

Preferably, the device 1 comprises a first and a second break wall, identified in the illustrations with reference numerals 20a and 20b respectively, which are arranged in succession to each other strafing from the third filtering element 10 towards the drawing union 15, where the passage gap 21b defined by the second break wall 20b is arranged higher than the passage gap 21a defined by the first break wall 20a.

The break walls 20a and 20b allow retaining lipids and white blood cells present in the blood and which collect in the upper layer of the blood itself in the second collecting volume 11b.

The appendix 18 and the recess 19 are therefore interposed between the second break wall 20b and the sleeve 16, and make it possible to prevent the separated lipids and white blood cells from being aspirated through the sleeve 16 or ending inside the first collecting volume 11a, depending on the position taken by the sleeve itself, even in the case of maximum drawing of the blood contained in the second collecting volume 11b.

The operation of the present invention is as follows.

As can be easily understood on the basis of the description provided above, before using the device according to the invention, the operator connects the inlets 4, 5 and 6 to the respective blood conveying lines.

The intracavitary and extracavitary venous blood therefore enters the first filtering volume 8a, the second filtering volume 9a and the third filtering volume 10a respectively, and flows through the corresponding filtering elements 8, 9 and 10. Each type of blood is then individually filtered.

In the embodiment shown in FIGS. 10 to 13, the blood entering the second and third inlets 5 and 6 meets the separation means 23, enters the corresponding channels 25 and is conveyed towards the conveying element 26. The blood thus travels the flowing surface 27, which pushes it towards the corresponding filtering element 9, 10 and progressively drops inside the corresponding filtering volume 9a, 10a.

In the device 1 according to the first embodiment, the blood thus filtered flows inside the collecting volume 11 and then flows out of the outlet mouth 7.

In the second embodiment, on the other hand, the blood that flows through the first and the second filtering element 8 and 9 collects in the first collecting volume 11a, flowing out of the outlet mouth 7, while the blood that flows through the third filtering element 10 collects in the second collecting volume 11b, to be then drawn, after having passed the break walls 20a and 20b, through the drawing union 15 or through the outlet mouth 7 depending on the position of the sleeve 16. As mentioned above, due to the sedimentation of the blood contained in the second collecting volume 11b, the break walls 20a and 20b allow retaining the lipids and white blood cells present therein.

It has in practice been found that the described invention achieves the intended objects and in particular the fact is emphasized that the device of the present invention allows using a specific filtering element for each type of blood to be filtered. This allows the filtration step to be optimized according to the properties of the blood to be filtered, thus improving the quality of the filtered blood with respect to known devices.

The separation wall in the second embodiment allows to further separate the blood components by retaining the lipids and white blood cells present therein.

The invention claimed is:

1. A blood filtering device, comprising:
   a casing defining a containment volume and provided with at least a first inlet for the venous blood, at least a second inlet for the intracavitary blood, at least a third inlet for the extra cavitary blood and at least an outlet mouth for the blood;

blood filtering means which are housed inside said containment volume and delimiting at least one filtering volume communicating with said blood inlets and at least one collecting volume communicating with said outlet mouth;

wherein said filtering means comprise:

at least a first filtering element defining a closed profile and delimiting a first filtering volume communicating with said first inlet;

at least a second filtering element defining a closed profile and delimiting a second filtering volume communicating with said second inlet; and at least a third filtering element defining a closed profile and delimiting a third filtering volume communicating with said third inlet;

wherein said filtering elements are separated and distinct from each other, and wherein the device further comprises a plurality of said second and/or third inlets and wherein the device further comprises blood separation means located at at least one of the second and third inlets and communicating with the corresponding filtering volume.

2. The device according to claim 1, wherein said inlets are defined at the upper portion of said casing.

3. The device according to claim 1, wherein said outlet mouth is defined at the bottom wall of said casing.

4. The device according to claim 1, wherein said filtering volumes correspond to the inner volume defined by each filtering element and that said collecting volume is arranged externally to said filtering elements.

5. The device according to claim 1, wherein said second and third filtering element are arranged side by side.

6. The device according to claim 5, wherein said first filtering element is interposed between said outlet mouth and said second and third filtering element.

7. The device according to claim 1, wherein said separation means comprise at least a body on which are defined a plurality of channels having curvilinear extension, where each of said channels is adapted to receive the blood flowing from a respective inlet to convey the received blood flowing from a peripheral area towards the center.

8. The device according to claim 7, wherein said channels have a converging section from the edge towards the center of said body.

9. The device according to claim 1, wherein inside at least one of said second and said third filtering element, at least one conveying element is housed which is adapted to guide the blood along a predefined path.

10. The device according to claim 9, wherein said conveying element is substantially screw-shaped.

11. A blood filtering device comprising:

a casing defining a containment volume and provided with at least a first inlet for the venous blood, at least a second inlet for the intracavitary blood, at least a third inlet for the extra cavitary blood and at least an outlet mouth for the blood;

blood filtering means which are housed inside said containment volume and delimiting at least one filtering volume communication with said blood inlets and at least one collecting volume communicating with said outlet mouth;

wherein said filtering means comprise:

at least a first filtering element defining a closed profile and delimiting a first filtering volume communicating with said first inlet;

at least a second filtering element defining a closed profile and delimiting a second filtering volume communicating with said second inlet;

at least a third filtering element defining a closed profile and delimiting a third filtering volume communicating with said third inlet;

wherein said filtering elements are separated and distinct from each other, wherein inside at least one of said second and said third filtering element, at least one conveying element is housed which is adapted to guide the blood along a predefined path, and wherein said conveying element has a blood flowing surface which defines a substantially helical path and the side edge of which is located at the internal wall of the corresponding filtering element.

12. The device according to claim 9, wherein the device further comprises a plurality of said second and/or third inlets and wherein the device further comprises blood separation means located at at least one of the second and third inlets and communicating with the corresponding filtering volume, and wherein said conveying element is arranged below said separation means.

13. The device according to claim 12, wherein said conveying element is interposed between said separation means and the bottom wall of said casing.

14. The device according to claim 1, wherein said collecting volume surrounds externally each of said filtering elements without interruption.

15. A blood filtering device comprising:

a casing defining a containment volume and provided with at least a first inlet for the venous blood, at least a second inlet for the intracavitary blood, at least a third inlet for the extra cavitary blood and at least an outlet mouth for the blood;

blood filtering means with are housed inside said containment volume and delimiting at least one filtering volume communicating with said blood inlets and at least one collecting volume communicating with said outlet mouth;

wherein said filtering means comprise;

at least a first filtering element defining a closed profile and delimiting a first filtering volume communicating with said first inlet;

at least a second filtering element defining a closed profile and delimiting a second filtering volume communicating with said second inlet;

at least a third filtering element defining a closed profile and delimiting a third filtering volume communication with said third inlet;

wherein said filtering elements are separated and distinct from each other, and wherein the device further comprises at least one separation wall positioned inside said collecting volume and operating in conjunction with said casing to divide the collecting volume itself into a first collecting volume surrounding said first and second filtering element and communicating with said outlet mouth and into a second collecting volume surrounding said third filtering element.

16. The device according to claim 15, wherein the device further comprises at least two break walls housed inside said second collecting volume, interposed between said third filtering element and said drawing union and defining respective passage gaps of the filtered blood positioned at different heights with respect to the bottom wall of said casing.

17. The device according to claim 16, wherein said break walls comprise a first break wall and a second break wall arranged in succession to one another from said third filtering element towards said drawing union and wherein the passage gap defined by said second break wall is arranged higher than the passage gap defined by said first break wall.

18. The device according to claim 15, wherein said drawing union comprises at least one sleeve accessible from the outside, provided with at least one or more first openings positionable in communication with said second collecting volume and provided with at least a second opening for the passage of blood, and wherein said separation wall comprises at least one passage communicating with said first collecting volume, said sleeve being operable in rotation between an opening configuration, in which at least one of said first openings is placed in communication with said second collecting volume and said second opening is located at said passage, so as to place said first collecting volume in communication with said second collecting volume, and a closure configuration, in which at least one of said first openings is placed in communication with said second collecting volume and said second opening is isolated from said passage.

19. The device according to claim 18, wherein the device further comprises at least an appendix extending from said bottom wall, housed inside said second collecting volume and provided with at least one recess, and wherein said sleeve has at least two of said first openings and at least a second opening, in the opening position of said sleeve one of said first openings being positioned at said recess and said second opening at said passage, in the closing position the other of said first openings being arranged at said recess and said second opening being closed.

20. The device according to claim 1, wherein said filtering elements have a tubular shape and said first filtering element has greater longitudinal extension than said second and third filtering element.

* * * * *